United States Patent [19]

Elekes et al.

[11] 4,419,522
[45] Dec. 6, 1983

[54] HEXITOLS CONTAINING FREE CARBOXY GROUPS AND A PROCESS FOR THE PREPARATION THEREOF

[75] Inventors: Ilona Elekes; László Institoris; Kálmán Medzihradsz; László Ötvös; Hedvig Medzihradszky-Schweiger; Katalin De Gleria; János Sugar; Somfai Relle; Sándor Eckhardt; Ivan Hidy; Sandor Kérpel-Fronius, all of Budapest, Hungary

[73] Assignee: Chinoin Gyogyszer Vegyeszeti Termekek Gyara Rt., Budapest, Hungary

[21] Appl. No.: 315,182

[22] Filed: Oct. 26, 1981

[30] Foreign Application Priority Data

Nov. 4, 1980 [HU] Hungary ............................. 2649/80

[51] Int. Cl.³ .................. C07D 303/16; C07C 69/657; C07C 69/653; C07C 69/65; C07C 69/635; C07C 69/63; A61K 31/335
[52] U.S. Cl. .................................... 549/557; 560/197; 560/111; 560/104; 260/405.5; 260/408; 260/410.6; 542/427; 424/278; 424/308; 424/312; 424/313
[58] Field of Search ...................... 560/197, 111, 104; 260/348.61, 348.62, 408, 410.6, 405.5; 424/278, 313, 312; 549/557; 542/427

[56] References Cited

PUBLICATIONS

Susan Somfai-Relle et al., "Proceedings of the 10th International Congress of Chemotherapy", vol. II, Sep. 10-23, 1977, pp. 1302-1303.
E. J. Hidvegi et al., Biochem. Pharmacol. (1976), vol. 25 (15), pp. 1705-1710.
J. F. W. McOmie, Protective Groups in Organic Chemistry, (1973), pp. 109, 196-197.

*Primary Examiner*—Norma S. Milestone
*Attorney, Agent, or Firm*—Karl F. Ross; Herbert Dubno

[57] ABSTRACT

The invention relates to new hexitols having the general formula (I) and (II),

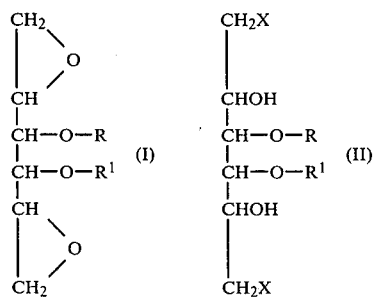

wherein
the hexitol skeleton is dulcitol, mannitol or iditol,
X represents halogen, preferably bromine,
R is a saturated or unsaturated $C_{4-10}$ alkylcarbonyl group which also contains a free carboxy group, and
$R^1$ is hydrogen, a saturated or unsaturated $C_{4-10}$ alkylcarbonyl group which also contains a free carboxy group, a saturated or unsaturated $C_{2-10}$ alkylcarbonyl group, a saturated or unsaturated $C_{4-10}$ alkylcarbonyl group which also contains an alkoxycarbonyl group, or a saturated or unsaturated $C_{8-10}$ aralkylcarbonyl group, and salts of these compounds. The new compounds according to the invention have tumor-inhibiting affects.

The above compounds are prepared according to the invention so that
(a) a compound of the general formula (IX), wherein the hexitol skeleton is dulcitol, mannitol or iditol,
Q is a saturated or unsaturated $C_{11-17}$ alkylcarbonyl group which also contains a benzyloxycarbonyl group, and
$Q^1$ is hydrogen, a saturated or unsaturated $C_{2-10}$ alkylcarbonyl group, a saturated or unsaturated $C_{4-10}$ alkylcarbonyl group which also contains an alkoxycarbonyl group, a saturated or unsaturated $C_{11-17}$ alkylcarbonyl group which also contains a benzyloxycarbonyl group, or a saturated or unsaturated $C_{8-10}$ aralkylcarbonyl group,
is hydrogenated in an anhydrous solvent in the presence of a weakly active catalyst which does not affect the epoxide ring, or
(b) a 1,2-5,6-dianhydrohexitol of the general formula (X), wherein the hexitol skeleton is dulcitol, mannitol or iditol, is reacted with a dicarboxylic acid anhydride of the general formula (XI), wherein A is a $C_{2-10}$ alkyl, aralkyl or aryl group, or
(c) a compound of the general formula (I) is reacted with an alkali halide and/or hydrogen halide.

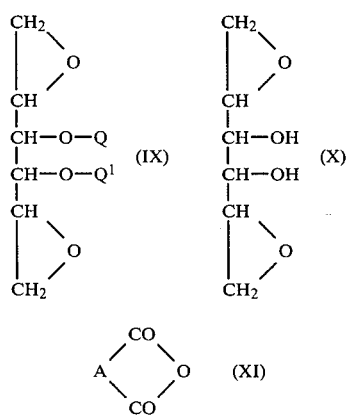

11 Claims, No Drawings

HEXITOLS CONTAINING FREE CARBOXY GROUPS AND A PROCESS FOR THE PREPARATION THEREOF

The invention relates to new hexitols having the formulae (I) and (II),

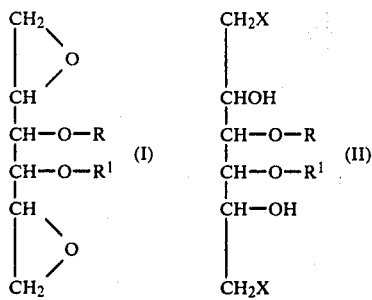

wherein
the hexitol skeleton is dulcitol, mannitol or iditol,
X represents halogen, preferably bromine,
R is a saturated or unsaturated $C_{4-10}$ alkylcarbonyl group which also contains a free carboxy group, and
$R^1$ is hydrogen, a saturated or unsaturated $C_{4-10}$ alkylcarbonyl group which also contains a free carboxy group, a saturated or unsaturated $C_{2-10}$ alkylcarbonyl group, a saturated or unsaturated $C_{4-10}$ alkylcarbonyl group which also contains an alkoxycarbonyl group, or a saturated or unsaturated $C_{8-10}$ aralkylcarbonyl group,
and salts thereof having tumor inhibiting effects. The invention also relates to pharmaceutical compositions containing the above new compounds as active agents, furthermore to a process for the preparation of the new compounds and the pharmaceutical compositions which contain them.

The new compounds are prepared according to the invention as follows:

(a) to prepare a compound of the formula (I), a compound of the formula (IX),

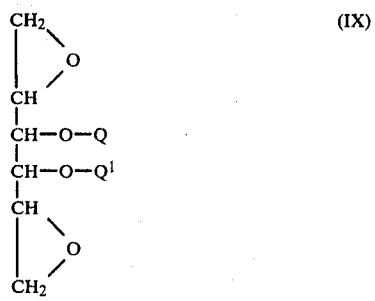

wherein
the hexitol skeleton is dulcitol, mannitol or iditol,
Q is a saturated or unsaturated $C_{11-17}$ alkylcarbonyl group which also contains a benzyloxycarbonyl group, and
$Q^1$ is hydrogen, a saturated or unsaturated $C_{2-10}$ alkylcarbonyl group, a saturated or unsaturated $C_{4-10}$ alkylcarbonyl group which also contains an alkoxycarbonyl group, a saturated or unsaturated $C_{11-17}$ alkylcarbonyl group which also contains a benzyloxycarbonyl group, or a saturated or unsaturated $C_{8-10}$ aralkylcarbonyl group,
is hydrogenated in an anhydrous solvent in the presence of palladium-on-carbon catalyst or any other weakly active catalyst which does not affect the epoxide rings, or (b) to prepare a compound of the formula (I), a 1,2-5,6-dianhydrohexitol of the formula (X),

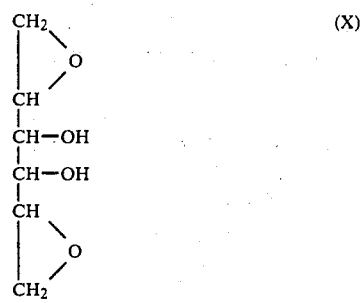

wherein the hexitol skeleton is dulcitol, mannitol or iditol, is reacted with a dicarboxylic acid anhydride of the formula (XI), $$\begin{array}{c} CO \\ A \diamond O \\ CO \end{array} \quad (XI)$$

wherein A is a $C_{2-10}$ alkyl, aryl or aralkyl group, preferably in an anhydrous medium in the presence of a base, or (c) to prepare a compound of the formula (II), a compound of the formula (I) is reacted with an alkali halide and/or hydrogen halide.

If desired, a compound of the formula (I) or (II) is converted into its salt.

The term "a saturated or unsaturated $C_{4-10}$ alkylcarbonyl group also containing a free carboxy group" refers to e.g. carboxybutyryl, carboxyvaleryl, carboxycaproyl, carboxycapryl, carboxypelargonyl, carboxyacryloyl, carboxycrotonyl and carboxymethacryloyl groups, of which the carboxypropionyl group is preferred.

The term "a saturated or unsaturated $C_{2-10}$ alkylcarbonyl group" refers to e.g. propionyl, butyryl, valeryl, caproyl, capryl, pelargonyl, caprinoyl, acryloyl, crotonyl and methacryloyl. A preferred alkylcarbonyl group is acetyl.

Of the saturated or unsaturated $C_{4-10}$ alkylcarbonyl groups which also contain an alkoxycarbonyl group e.g. the following are to be mentioned: carbethoxypropionyl, carbopropoxypropionyl, carbobutoxypropionyl, carbopentoxypropionyl, carbohexyloxypropionyl, carbomethoxyacryloyl, carbomethoxycrotonyl and carbomethoxymethacryloyl groups. A preferred member of these groups is the carbomethoxypropionyl group.

The term "a saturated or unsaturated $C_{8-10}$ aralkylcarbonyl group" refers to e.g. phenylacetyl, phenylbutyryl, phenylacryloyl, phenylcrotonyl and phenylpropionyl groups, of which phenylpropionyl is the most preferred.

The term "a saturated or unsaturated $C_{11-17}$ alkylcarbonyl group also containing a benzyloxycarbonyl group" refers to e.g. benzyloxycarbonyl-butyryl, benzyloxycarbonylvaleryl, benzyloxycarbonyl-caproyl, benzyloxycarbonyl-capryl, benzyloxycarbonyl-pelargonyl, benzyloxycarbonyl-acryloyl, benzyloxycarbonyl-crotonyl, benzyloxycarbonyl-methacryloyl and benzyloxycarbonyl-propionyl groups, of which benzyloxycarbonylpropionyl is the most preferred.

Of the salts of the new compounds having the formulae (I) and (II) salts formed with alkali metals and alkaline earth metals, preferably lithium, potassium, sodium, calcium and magnesium salts, furthermore salts formed with organic bases, preferably with amines, particularly with tris(hydroxymethylamino)-methane, are to be mentioned.

The following compounds can be applied most preferably as active agents in pharmaceutical compositions:

1,2-5,6-dianhydro-3,4-bis(β-carboxypropionyl)-dulcitol and salts thereof, 1,2-5,6-dianhydro-3-(β-carboxypropionyl)-dulcitol and salts thereof, 1,2-5,6-dianhydro-3-(β-carboxypropionyl)-4-acetyl-dulcitol and salts thereof, 1,2-5,6-dianhydro-3-(β-carboxypropionyl)-4-(β-carbomethoxypropionyl)-dulcitol and salts thereof, 1,2-5,6-dianhydro-3-(β-carboxypropionyl)-4-(β-phenylpropionyl)-dulcitol and salts thereof, 1,6-dideoxy-1,6-dibromo-3,4-bis(β-carboxypropionyl)-dulcitol and salts thereof, 1,2-5,6-dianhydro-3-(β-carboxypropionyl)-dulcitol and salts thereof, furthermore 1,2-5,6-dianhydro-3,4-bis(β-carboxypropionyl)-dulcitol and salts thereof.

Derivatives of 3,4-diacylated dianhydro-hexitols which contain carboxylate groups have already been described in the British patent specification No. 1,490,649. These substances are, however, difficult to convert into the respective free carboxylic acid derivatives either by alkaline or by enzymatic hydrolysis, since the ester bonds attached directly to the hexitol skeleton are also susceptible hydrolysis at to these reaction conditions.

According to a preferred method of the invention 1,2-5,6-dianhydro-3,5-bis(β-benzyloxycarbonyl-propionyl)-dulcitol of the formula (III),

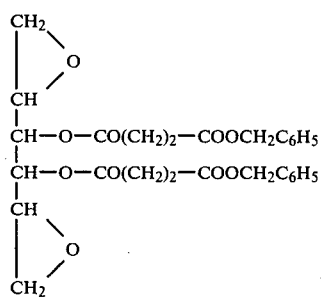

a compound prepared in a known manner (see the British patent specification No. 1,490,649), is hydrogenated in dry methanol in the presence of palladium-on-carbon catalyst until the uptake of the calculated amount (2 moles) of hydrogen. This requires about one or two hours. 1,2-5,6-Dianhydro-3,4-bis(β-carboxypropionyl)-dulcitol (which can also be termed as 1,2-5,6-dianhydro-3,4-disuccinyl-dulcitol) of the formula (IV),

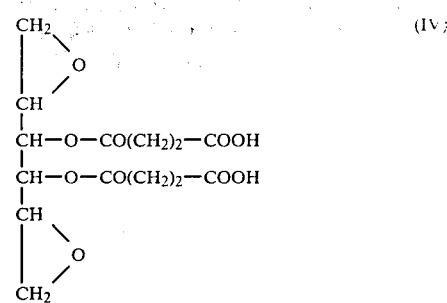

which can be crystallized from a mixture of tetrahydrofuran and petroleum ether, is obtained with an excellent yield.

Hydrogenation can also be performed in other solvent media. When selecting the hydrogenating catalyst care should be taken as to its activity; catalysts which are active enough to split the epoxide rings as well cannot be used in the process.

Similarly can be obtained 1,2-5,6-dianhydro-3-(β-carboxypropionyl)-dulcitol of the formula (V)

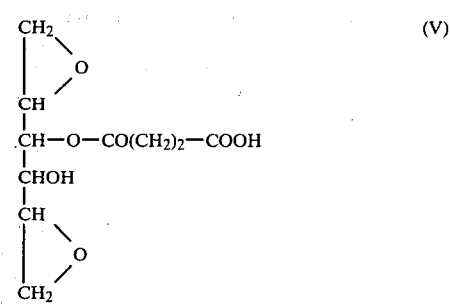

from 1,2-5,6-dianhydro-3-(β-benzyloxycarbonyl-propionyl)-dulcitol, 1,2-5,6-dianhydro-3-(β-carboxypropionyl)-4-acetyl-dulcitol of the formula (VI)

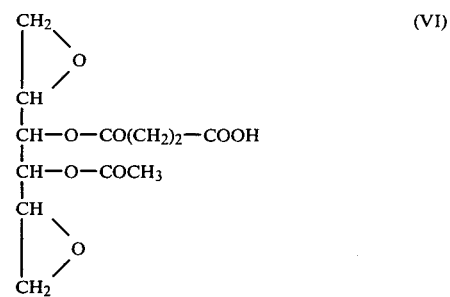

from 1,2-5,6-dianhydro-3-(β-benzyloxycarbonyl-propionyl)-4-acetyl-dulcitol, 1,2-5,6-dianhydro-3-(β-carboxypropionyl)-4-(β-carbomethoxypropionyl)-dulcitol of the formula (VII)

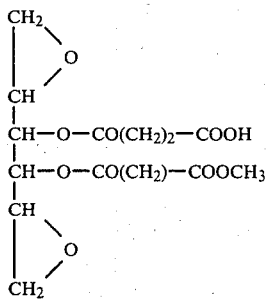

from 1,2-5,6-dianhydro-3-(β-benzyloxycarbonyl-propionyl)-4-(β-carbomethoxypropionyl)-dulcitol, and 1,2-5,6-dianhydro-3-(β-carboxypropionyl)-4-(β-phenylpropionyl)-dulcitol of the formula (VIII)

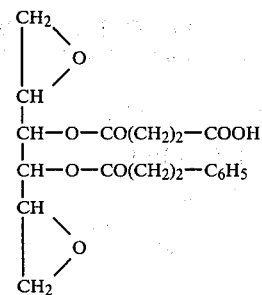

from 1,2-5,6-dianhydro-3-(β-benzyloxycarbonyl-propionyl)-4-(β-phenylpropionyl)-dulcitol.

The D-iditol and D-mannitol analogs of the D-dulcitol compounds having the formulae (IV) to (VIII) can be prepared similarly from the respective benzyl esters.

The β-carboxypropionyl derivatives can also be prepared according to the invention by subjecting the respective dianhydro-hexitols to direct acylation with succinic anhydride.

One proceeds preferably so that a compound of the formula (X), e.g. 1,2-5,6-dianhydro-dulcitol, is reacted with succinic anhydride in an anhydrous solvent in the presence of a tertiary base. The substance, isolated from the reaction mixture with almost quantitative yield, is subjected then to column chromatography on silica gel to separate the monosuccinyl and disuccinyl compounds from each other. These compounds are identical to those obtained by the hydrogenolysis of the respective benzyl esters.

The dideoxy-dihalo derivatives of the above dianhydro compounds are prepared according to the invention by treating the dianhydro-hexitol compounds containing a free carboxy group with potassium bromide and hydrogen bromide. The dihalo compounds are crystalline substances easy to characterize and identify, and form in the reaction with a yield of almost 100%.

The dianhydro-disuccinyl-hexitols prepared according to the invention are relatively poorly soluble in water, and this holds even to a greater extent for the dihalo-dideoxy-disuccinyl-hexitols. In order to increase their solubilities in water, these compounds were converted into their salts formed with alkali metals, alkaline earth metals and organic bases.

Compared to the known dianhydro-hexitols and dideoxy-dihalo-hexitols, which are either unsubstituted or have only hydrophobic substituents, the new dianhydro-hexitols and dideoxy-dihalo-hexitols according to the invention, which contain a free carboxy group, have far more favorable therapeutical indices. In order to illustrate this fact, the characteristic activity data of 1,2-5,6-dianhydro-dulcitol (DAD) and 1,2-5,6-dianhydro-3,4-diacetyl dulcitol (diAcDAD), known from the literature, are compared to those of 1,2-5,6-dianhydro-3,4-bis(β-carboxypropionyl)-dulcitol (diSuDAD), a compound according to the invention. The data, observed on Walker i.m. carcinosarcoma, S-180 sarcoma and $P_{388}$ leukaemia, are listed in Table 1 below.

TABLE 1

| Compound | $LD_{50}$ mg/kg | $LD_{10}$ mg/kg | $LD_{10}$ μM/kg | $ED_{90}$ μM/kg | $\dfrac{LD_{10}}{ED_{90}}$ |
| --- | --- | --- | --- | --- | --- |
| DAD | 15 | 10 | 68 | 16 | 4 |
| diAcDAD | 34 | 25.5 | 110 | 15 | 7 |
| diSuDAD | 630 | 190 | 550 | 14 | 40 |

The new acylated dianhydro-hexitol compounds according to the invention can be utilized in the therapy for inhibiting tumours in a number of ways.

The new compounds can be converted into compositions for oral administration, e.g. tablets, either as such or in combination with conventional auxiliary agents of making such compositions (e.g. starch, lactose, talc, etc.). Tablets for oral administration may contain e.g. 20 to 90% of the active ingredient.

The compounds can also be converted into solutions or suspensions for injection purposes, utilizing water or a physiologically inert organic solvent (such as various glycols, etc.). The solutions, which can be administered e.g. as intravenous, intramuscular, intraperitoneal or intracavital injections, may contain e.g. 1 to 10% of active agent, whereas the suspensions, which can be administered e.g. as intramuscular, intraperitoneal or intracavital injections, may contain e.g. 1 to 70% of active agent.

The new compounds can also be applied in the therapy as locally applicable compositions for the treatment of skin or operation sites, either alone or in combination with conventional antibacterial and/or wound-healing agents, such as sulfonamides, corticoids, vitamins, etc.

The pharmaceutical compositions according to the invention may contain a single active agent of the formula (I) or (II) or a mixture of such active agents.

The invention is elucidated in detail by the aid of the following non-limiting Examples. All of the starting substances utilized are known compounds.

EXAMPLE 1

Preparation of a palladium-on-carbon catalyst (a) 0.2 g of palladium chloride are dissolved in 2 ml of distilled 5.7 normal hydrochloric acid under heating, the solution is diluted to the five-fold with water, thereafter 0.9 g of activated carbon (Merck, p.a.) are added, and the suspension is boiled for some minutes. The suspension is cooled and then rendered alkaline (pH=9) with 20% aqueous sodium hydroxide solution under shaking, so that the solution above the solids becomes completely colorless.

(b) 0.2 g of palladium chloride are dissolved in 2 ml of distilled 5.7 normal hydrochloric acid under heating, the solution is diluted with 80 ml of distilled water, and 9.0 g of activated carbon (Merck, p.a.) are added. The resulting suspension is rendered alkaline as described in point (a) above.

The suspensions obtained according to points (a) and (b) are admixed, blended thoroughly, the catalyst is filtered off, washed chloride-free on the filter, and then washed with 200 ml of a 1% acetic acid solution. The wet catalyst is dried in a desiccator over concentrated sulfuric acid.

EXAMPLE 2

Preparation of
1,2-5,6-dianhydro-3,4-bis($\beta$-carboxypropionyl)-dulcitol 1.6 g (3 mmoles) of 1,2-5,6-dianhydro-3,4-bis($\beta$-benzyloxycarbonyl-propionyl)-dulcitol are dissolved in 150 ml of dry methanol, 0.3 g of a catalyst prepared according to Example 1 are added to the solution, and the resulting mixture is hydrogenated until the uptake of the theoretical amount of hydrogen. This requires about 1.5 hours. The catalyst is filtered off, the solution is evaporated in vacuo, the resulting white, crystalline substance is suspended in ether, and the solids are filtered off. The substance is recrystallized from a mixture of ether and petroleum ether to obtain 1.0 g (96%) of 1,2-5,6-dianhydro-3,4-bis($\beta$-carboxypropionyl)-dulcitol; m.p.: 138°–139° C. The product is uniform upon examining it by layer chromatography ($R_f=0.15$; run with a 9:2 mixture of benzene and methanol and visualized with p-nitrobenzylpyridine).

Analysis: Calculated for $C_{14}H_{18}O_{10}$(346.29): C: 48.78%, H: 5.73%, O: 45.49%; found: C: 48.35%, H: 5.25%, O: 46.60%.

Equivalent weight: calculated: 173, found: 180.

IR spectrum: 3350 cm$^{-1}$ (carboxy), 1235 cm$^{-1}$ (epoxy, benzyl and hydroxy bands do not appear.

Solubility: the compound dissolves well in alcohol and tetrahydrofuran, and is poorly soluble in ether and water.

EXAMPLE 3

Preparation of
1,2-5,6-dianhydro-3-($\beta$-carboxypropionyl)-dulcitol 2.0 g (6 mmoles) of 1,2-5,6-dianhydro-3-($\beta$-benzyloxycarbony-propionyl)-dulcitol are dissolved in 30 ml of dry methanol, 0.4 g of a palladium-on-carbon catalyst, prepared as described in Example 1, are added, and the mixture is hydrogenated until the uptake of the calculated amount (144 ml) of hydrogen. The catalyst is filtered off, the filtrate is evaporated in vacuo, and the solid residue is recrystallized from a mixture of methanol and ether. 1.15 g (79%) of 1,2-5,6-dianhydro-3-($\beta$-carboxypropionyl)-dulcitol are obtained; m.p.: 77°–78° C. The product is uniform upon examining it by layer chromatography ($R_f=0.1$ or 0.5; run with a 6:4 mixture of ethyl acetate and cyclohexane or a 8:2 mixture of benzene and methanol and visualized with p-nitrobenzyl-pyridine).

Analysis: calculated for $C_{10}H_{14}O_7$ (246.22): C: 48.78%, H: 5.73%, O: 45.49%; found: C: 48.60%, H: 5.33%, O: 45.58%.

Equivalent weight: calculated: 246, found: 250.

IR spectrum: 3600–2950 cm$^{-1}$ (broad band referring to carboxy and hydroxy groups), 2940 cm$^{-1}$ (aliphatic CH), 1740 cm$^{-1}$ (ester), 1220 cm$^{-1}$ (epoxy).

EXAMPLE 4

Preparation of
1,2-5,6-dianhydro-3-($\beta$-carboxypropionyl)-4-acetyl-dulcitol 3.78 g (10 mmoles) of 1,2-5,6-dianhydro-3-($\beta$-benzyloxycarbonyl-propionyl)-4-acetyl-dulcitol are hydrogenated as described in Example 2 until the uptake of hydrogen stops. The catalyst is filtered off, the filtrate is evaporated in vacuo, and the crystalline residue is recrystallized from a mixture of tetrahydrofuran and ethyl acetate. 2.5 g (88%) of 1,2-5,6-dianhydro-3-($\beta$-carboxypropionyl)-4-acetyl-dulcitol are obtained; m.p.: 134° C. The product is uniform upon examining it by layer chromatography ($R_f=0.2$ or 0.6; run with a 6:4 mixture of ethyl acetate and cyclohexane or a 8:2 mixture of benzene and methanol and visualized with p-nitrobenzyl-pyridine).

Analysis: calculated for $C_{12}H_{16}O_8$ (288.26): C: 50.00%, H: 5.59%, O: 44.40%; found: C: 49.48%, H: 5.26%, O: 44.70%.

Equivalent weight: calculated: 288, found: 296.

EXAMPLE 5

Preparation of
1,2-5,6-dianhydro-3-($\beta$-carboxypropionyl)-4-($\beta$-carbomethoxy-propionyl)-dulcitol 4.50 g (10 mmoles) of 1,2-5,6-dianhydro-3-($\beta$-benzyloxycarbonyl)-propionyl)-4-($\beta$-carbomethoxy-propionyl)-dulcitol are hydrogenated as described in Example 2 until the uptake of the calculated amount of hydrogen. The catalyst is filtered off, and the solvent is removed from the filtrate. 3.1 g (86%) of crystalline 1,2-5,6-dianhydro-3-($\beta$-carboxypropionyl)-4-($\beta$-carbomethoxy-propionyl)-dulcitol are obtained; m.p.: 87°–89° C. The product is uniform upon examining it by layer chromatography ($R_f=0.25$ or 0.4; run with a 6:4 mixture of ethyl acetate and cyclohexane or a 8:2 mixture of benzene and methanol).

Analysis: calculated for $C_{15}H_{20}O_{10}$ (362.34): C: 49.72%, H: 6.12%, O: 44.16%; found: C: 49.87%, H: 5.39%, O: 43.91%.

Equivalent weight: calculated: 362, found: 363.

EXAMPLE 6

Preparation of
1,2-5,6-dianhydro-3-($\beta$-carboxypropionyl)-4-($\beta$-phenylpropionyl)-dulcitol 4.68 g (10 mmoles) of 1,2-5,6-dianhydro-3-($\beta$-benzyloxycarbonyl)-propionyl)-4-($\beta$-phenylpropionyl)-dulcitol are hydrogenated as described in Example 2. The catalyst is filtered off and the solvent is removed from the filtrate to obtain 3.3 g (84%) of crystalline 1,2-5,6-dianhydro-3-($\beta$-carboxypropionyl)-4-($\beta$-phenylpropionyl)-dulcitol, m.p.: 80° C. The product is uniform upon examining it by layer chromatography ($R_f=0.3$ or 0.7; run with a 6:4 mixture of ethyl acetate and cyclohexane or a 8:2 mixture of benzene and methanol).

Analysis: calculated for $C_{19}H_{22}O_8$ (378.38): C: 60.31%, H: 5.86%, O: 33.83%; found: C: 60.60%, H: 5.49%, O: 34.50%.

Equivalent weight: calculated: 378; found: 390.

EXAMPLE 7

Preparation of 1,6-dideoxy-1,6-dibromo-3,4-bis($\beta$-carboxypropionyl)-dulcitol 0.365 g (1 mmole) of 1,2-5,6-dianhydro-3,4-bis($\beta$-carboxypropionyl)-dulcitol are dissolved in 5 ml of methanol, and a solution of 1.2 g (10 mmoles) of potassium bromide in 5 ml of water is added. Thereafter a mixture of 1 ml of a 48% hydrobromic acid and 0.5 ml of water is added dropwise to the mixture within 10 minutes under constant stirring. After stirring the mixture at room temperature for an additional 0.5 hours a clear solution is obtained, and after another 2 hours a white, crystalline substance starts to separate. The separated substance is filtered off and washed with distilled water until neutral. 0.460 g (90%) of 1,6-dideoxy-1,6-dibromo-3,4-bis($\beta$-carboxypropionyl)-dulcitol are obtained; m.p.: 165° C. The product is uniform upon examining it by layer chromatography ($R_f=0.05$; run with a 9:2 mixture of benzene and methanol and visualized with p-nitrobenzyl-pyridine).

Analysis: calculated for $C_{14}H_{20}O_{10}Br_2$ (508.13): C: 33.09%, H: 3.97%, O: 31.49%, Br: 31.45%; found: C: 33.42%, H: 4.00%, O: 31.23%, Br: 31.50%.

Equivalent weight: calculated: 254, found: 256.

EXAMPLE 8

Acylation of 1,2-5,6-dianhydro-dulcitol with succinic anhydride 1.46 g (10 mmoles) of 1,2-5,6-dianhydro-dulcitol are dissolved in 20 ml of dry ethyl acetate, 5 ml of pyridine are added to the solution, and then 2.0 g (20 mmoles) of succinic anhydride are added in small portions to the mixture under constant stirring. The mixture is warmed to 45° C. and stirred at this temperature for an additional 8 hours. The solvent is distilled off in vacuo, the residue is taken up in a mixture of ethyl acetate and water, and the resulting mixture is acidified cautiously, under ice cooling, to pH 4 to 5. The organic phase is separated, washed with water, dried and evaporated. 2.5 g of a solid residue are obtained, which corresponds to a quantitative yield when calculated as monosuccinyl-dianhydro-dulcitol.

The resulting crude substance is subjected to chromatography on a silica gel column, applying a 1:1 v/v mixture of methanol and ethyl acetate as eluting agent. The fractions which contain pure products are combined, the solution is evaporated in vacuo, and the resulting solid is recrystallized from a mixture of ether and petroleum ether and then from a mixture of methanol and ether. 1.8 g of 1,2-5,6-dianhydro-3-($\beta$-carboxypropionyl)-dulcitol and 0.4 g of 1,2-5,6-dianhydro-3,4-bis($\beta$-carboxypropionyl)-dulcitol are obtained. The physical constants of these compounds are identical with those of the products obtained according to Examples 2 and 3.

EXAMPLE 9

Preparation of the TRIS-salt of 1,2-5,6-dianhydro-3,4-bis($\beta$-carboxypropionyl)-dulcitol.

3.46 g (10 mmoles) of 1,2-5,6-dianhydro-3,4-bis($\beta$-carboxypropionyl)-dulcitol are dissolved in 20 ml of 96% ethanol under gentle warming, the solution is cooled, and a solution of 1.2 g (10 mmoles) of tris(hydroxymethylamino)-methane in 10 ml of water is added. The mixture is allowed to stand in a refrigerator, then the separated crystals are filtered off and dried in a desiccator. 3.7 g (80%) of the TRIS-salt are obtained.

EXAMPLE 10

Preparation of 1,2-5,6-dianhydro-3,4-bis($\beta$-carboxypropionyl)-mannitol 1.6 g (3 mmoles) of 1,2-5,6-dianhydro-3,4-bis($\beta$-benzyloxycarbonyl-propionyl)-mannitol are dissolved in 150 ml of tetrahydrofuran, 0.4 g of a catalyst, prepared as described in Example 1, are added to the solution, and the mixture is hydrogenated until the uptake of the calculated amount (288 ml) of hydrogen. The catalyst is filtered off, the solvent is distilled off in vacuo, and the solid residue is recrystallized from a mixture of ethyl acetate and petroleum ether. 0.85 g (82%) of 1,2-5,6-dianhydro-3,4-bis($\beta$-carboxypropionyl)-mannitol are obtained; m.p.: 125°–130° C. The hygroscopic, crystalline substance is uniform when examined by layer chromatography ($R_f=0.6$; run in a 1:1 mixture of tetrahydrofuran and methanol).

Analysis: calculated for $C_{14}H_{18}O_{10}$ (346.29): C: 48.56%, H: 5.24%, O: 46.20%; found: C: 48.35%, H: 5.48%, O: 46.56%.

EXAMPLE 11

Preparation of 1,2-5,6-dianhydro-3-($\beta$-carboxypropionyl)-mannitol 2 g (6 mmoles) of 1,2-5,6-dianhydro-3-($\beta$-benzyloxycarbonyl-propionyl)-mannitol are dissolved in 30 ml of tetrahydrofuran, 0.4 g of palladium-on-carbon catalyst, prepared as described in Example 1, are added, and the mixture is hydrogenated until the uptake of the calculated amount (144 ml) of hydrogen. The catalyst is filtered off and the solvent is evaporated in vacuo to obtain 1.13 g (78%) of 1,2-5,6-dianhydro-3-($\beta$-carboxypropionyl)-mannitol as a thick, viscous oil. The product is uniform when examined by layer chromatography ($R_f=0.8$; run in a 1:1 mixture of tetrahydrofuran and methanol).

Analysis: calculated for $C_{10}H_{14}O_7$ (246.22): C: 48.78%, H: 5.73%; found: C: 48.26%, H: 5.96%.

Equivalent weight: calculated: 246, found: 238.

EXAMPLE 12

Preparation of freeze-dried powder ampoulles containing 10 mg of 1,2-5,6-dianhydro-3,4-bis($\beta$-carboxypropionyl)-mannitol One powder ampoulle contains 10 mg of 1,2-5,6-dianhydro-3,4-bis($\beta$-carboxypropionyl)-mannitol;

one solvent ampoulle contains 300 mg of sorbitol+-distilled water for injection q.s. ad 2 ml.

The pharmaceutical compositions are prepared as follows:

50 g of pure (100%) 1,2-5,6-dianhydro-3,4-bis($\beta$-carboxypropionyl)-mannitol of pharmaceutical quality are filled into a calibrated vessel, 10 liters in volume, the active agent is dissolved in the vessel in 20° C. distilled water for injection purposes, free of carbon dioxide, and the contents of the flask is adjusted to the mark with distilled water of the same quality. Thereafter the solution is sterilized by filtration under aseptic conditions. 2 ml portions of the sterile solution are filled into ampoulles and subjected to freeze-drying in a conventional industrial apparatus. The frozen substance is sublimated at a hypoeutectic temperature, and the final drying step is performed at 30° C. Thereafter the ampoulles are stoppered with a rubber stopper and sealed with a metal band under sterile conditions, and then provided with an appropriate signature. The powder ampoulles are packaged with solvent ampoulles filled with 2 ml of a 15 w/v % aqueous sorbitol solution, prepared according to standard techniques.

EXAMPLE 13

Preparation of capsules containing 100 mg of 1,2-5,6-dianhydro-3,4-bis($\beta$-carboxypropionyl)-mannitol One capsule contains
100 mg of 1,2-5,6-dianhydro-3,4-bis($\beta$-carboxypropionyl)-mannitol
5 mg of Carbowax 6000 and
5 mg of talc Carbowax and talc are homogenized, the resulting fine, powdery homogenizate is admixed with the pure, crystalline active agent of pharmaceutical quality, and the resulting granules are filled into hard gelatine capsules. One capsule contains 110 mg of the granular mix.

EXAMPLE 14

Preparation of intestinosolvent capsules

The capsules prepared according to Example 13 are provided with an intenstinosolvent coating.

What we claim is:
1. A hexitol of the formula (I) or (II),

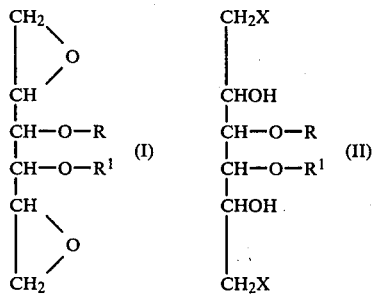

wherein
the hexitol skeleton is dulcitol, mannitol or iditol,
X represents halogen,
R is a saturated or unsaturated $C_{4-10}$ alkylcarbonyl group which also contains a free carboxy group, and
$R^1$ is hydrogen, a saturated or unsaturated $C_{4-10}$ alkylcarbonyl group which also contains a free carboxy group, a saturated or unsaturated $C_{2-10}$ alkylcarbonyl group, a saturated or unsaturated $C_{4-10}$ alkylcarbonyl group which also contains an alkoxycarbonyl group, or a saturated or unsaturated $C_{8-10}$ aralkylcarbonyl group,
or a pharmaceutically acceptable salt thereof.

2. 1,2-5,6-Dianhydro-3,4-bis($\beta$-carboxypropionyl)-dulcitol and salts thereof as defined in claim 1.
3. 1,2-5,6-Dianhydro-3-($\beta$-carboxypropionyl)-dulcitol and salts thereof as defined in claim 1.
4. 1,2-5,6-Dianhydro-3-($\beta$-carboxypropionyl)-4-acetyl-dulcitol and salts thereof as defined in claim 1.
5. 1,2-5,6-Dianhydro-3-($\beta$-carboxypropionyl)-4-($\beta$-carbomethoxypropionyl)-dulcitol and salts thereof as defined in claim 1.
6. 1,2-5,6-Dianhydro-3-($\beta$-carboxypropionyl)-4-($\beta$-phenylpropionyl-dulcitol and salts thereof as defined in claim 1.
7. 1,6-Dideoxy-1,6-dibromo-3,4-bis($\beta$-carboxypropionyl)-dulcitol and salts thereof as defined in claim 1.
8. 1,2-5,6-Dianhydro-3-($\beta$-carboxypropionyl)-mannitol and salts thereof as defined in claim 1.
9. 1,2-5,6-Dianhydro-3,4-bis($\beta$-carboxypropionyl)-mannitol and salts thereof as defined in claim 1.
10. A dulcitol of the formula (I)

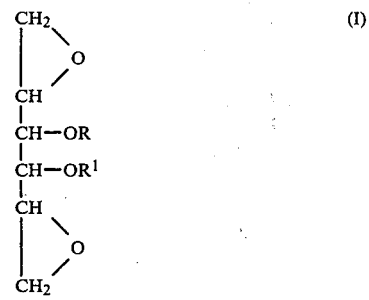

wherein
R is a saturated or unsaturated $C_4$–$C_{10}$ alkylcarbonyl group which also contains a free carboxy group, and
$R^1$ is hydrogen, a saturated or unsaturated $C_4$–$C_{10}$ alkylcarbonyl group which also contains a free carboxy group, a saturated or unsaturated $C_4$–$C_{10}$ alkylcarbonyl group which also contains an alkoxycarbonyl group, or a saturated or unsaturated $C_8$–$C_{10}$ aralkylcarbonyl group, or a pharmaceutically acceptable salt thereof.

11. A dulcitol of the formula (I)

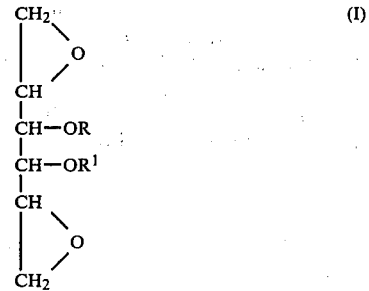

wherein
R is carboxypropionyl, and
$R^1$ is carboxypropionyl, acetyl, carbomethoxy-propionyl or phenylpropionyl, or a pharmaceutically acceptable salt thereof.

* * * * *